United States Patent
Volpe, Jr.

(10) Patent No.: US 7,354,380 B2
(45) Date of Patent: *Apr. 8, 2008

(54) HEART RATE MONITOR FOR CONTROLLING ENTERTAINMENT DEVICES

(76) Inventor: Joseph C. Volpe, Jr., 115 Jaffrey Rd., Malvern, PA (US) 19355

( * ) Notice: Subject to any disclaimer, the term of this patent is extended or adjusted under 35 U.S.C. 154(b) by 102 days.

This patent is subject to a terminal disclaimer.

(21) Appl. No.: 11/289,115

(22) Filed: Nov. 22, 2005

(65) Prior Publication Data

US 2006/0084551 A1   Apr. 20, 2006

Related U.S. Application Data

(63) Continuation-in-part of application No. PCT/US03/13397, filed on Apr. 23, 2003.

(60) Provisional application No. 60/689,042, filed on Jul. 5, 2005.

(51) Int. Cl.
    *A63B 21/00* (2006.01)
(52) U.S. Cl. .................. 482/4; 482/8; 600/519
(58) Field of Classification Search .......... 482/1–9, 482/37, 51, 54, 57, 900, 901, 902; 600/519, 600/481, 483, 486, 508, 514; 900/902
    See application file for complete search history.

(56) References Cited

U.S. PATENT DOCUMENTS

| | | | |
|---|---|---|---|
| 3,595,219 A | 7/1971 | Friedlander | |
| 3,863,626 A | 2/1975 | Huber | |
| 5,215,468 A * | 6/1993 | Lauffer et al. | 434/236 |
| 5,267,942 A * | 12/1993 | Saperston | 600/28 |
| 5,362,069 A | 11/1994 | Hall-Tipping | |
| 5,462,504 A | 10/1995 | Trulaske | |
| 5,474,090 A * | 12/1995 | Begun et al. | 600/520 |
| 5,524,637 A | 6/1996 | Erickson | |
| 5,527,239 A | 6/1996 | Abbondanza | |
| 5,888,172 A | 3/1999 | Andrus | |
| 5,921,891 A * | 7/1999 | Browne | 482/8 |
| 6,004,243 A * | 12/1999 | Ewert | 482/8 |
| 6,013,007 A * | 1/2000 | Root et al. | 482/8 |
| 6,142,913 A * | 11/2000 | Ewert | 482/8 |
| 6,230,047 B1 * | 5/2001 | McHugh | 600/519 |
| 6,251,048 B1 | 6/2001 | Kaufman | |
| 6,304,774 B1 | 10/2001 | Gorman | |
| 6,572,511 B1 * | 6/2003 | Volpe | 482/4 |
| 6,746,371 B1 * | 6/2004 | Brown et al. | 482/8 |
| 7,003,122 B2 * | 2/2006 | Chen | 381/67 |

(Continued)

*Primary Examiner*—Lori Amerson
*Assistant Examiner*—Sundhara M Ganesan
(74) *Attorney, Agent, or Firm*—Dann, Dorfman, Herrell and Skillman; Henry H. Skillman

(57) ABSTRACT

Described is a motivational fitness device, which controls the audio output of a television or audio component in response to the heart rate. The user must exercise in their specific heart rate target training range to keep their entertainment device turned on at an enjoyable volume. A heart rate sensing device relays heart rate to a processor unit. The processor receives and compares the user's heart rate to the specified target range and sends control signals (or not) to the entertainment device. If the user's heart rate drops below the target range, the volume of the audio output of their entertainment device will gradually decrease until the user reacquires their target. Conversely, if the user is exercising too vigorously, the volume will increase, motivating the user to reacquire their target heart rate range.

9 Claims, 6 Drawing Sheets

U.S. PATENT DOCUMENTS

| | | | |
|---|---|---|---|
| 7,177,672 B2 * | 2/2007 | Nissila | 600/519 |
| 2003/0171189 A1 * | 9/2003 | Kaufman | 482/8 |
| 2005/0202934 A1 * | 9/2005 | Olrik et al. | 482/8 |
| 2005/0233859 A1 * | 10/2005 | Takai et al. | 482/3 |

* cited by examiner

HEART RATE MONITOR FOR CONTROLLING ENTERTAINMENT DEVICES

RELATED APPLICATION

This application is a continuation-in-part application of PCT/US2003/013,397, filed Apr. 23, 2003, which is based on U.S. application Ser. No. 09/711,372 filed Nov. 10, 2000 (granted as U.S. Pat. No 6,572,511 on Jun. 3, 2003), and claiming priority of U.S. Application No. 60/165,011 filed Nov. 12, 1999. This application claims priority from U.S. Patent Application No. 60/689,042 filed Jul. 5, 2005.

BACKGROUND OF THE INVENTION

While the benefits of exercise are well known, it is often the case that one lacks the motivation to exercise regularly and at optimal intensity. Several attempts have been made to develop devices, which entertain or motivate a person during exercise. The prior art holds various examples of exercise intensity sensing devices connected to electronic devices. However, such equipment is bulky and expensive. Furthermore, a complex apparatus, which integrates an exercise device with a video apparatus or other audio/visual components to stimulate exercise, cannot be easily adapted to the existing base of exercise equipment found in the home. Some of the existing examples use proprietary audio/visual equipment such as variable speed video players or devices, which produce television type images. Some employ heart rate target training strategies. Thus, there is a need in the art for a simple, adaptable, inexpensive and less cumbersome device, which provides the user with effective motivational feedback to encourage optimal exercise.

U.S. Pat. No. 5,362,069 describes an exercise device/video game, which senses the speed of a pedaled exercise device and heart rate of the user. These signals are used to alter both the difficulty (resistance) of the exercise device and the play of the video game. This apparatus is dependent upon a fixed exercise device or one whereby ergonomic speed can be sensed. The entertainment form is active (interactive gaming).

U.S. Pat. No. 5,896,164 describes a video biofeedback apparatus that produces television displays that change with users psychophysiological parameters. The display is dependent on pre-recorded video signals on a videocassette. It does not offer entertainment as a motivational element.

U.S. Pat. No. 4,278,095 describes a pre-recorded variable speed video display, which is affected by the ergonomic speed of an exercise device (treadmill). It is dependent upon a variable speed video cassette player and a dedicated exercise machine. The entertainment form is passive but "canned" being limited to the prerecorded outdoor exercise scenes, which vary only in the speed of playback.

U.S. Pat. No. 5,779,596 describes the remote control of an electronic device with input signals generated by an exercise device fitted with a speed sensor. This is dependent on a fixed exercise device and/or ergonomic speed sensor and the entertainment device is limited to only two operational modes. It does not incorporate heart rate target training as a means of inducing optimal results.

U.S. Pat. No. 5,527,239 describes an exercise device capable of responding to user heart rate and adjusting the physical resistance of the fixed exercise device. The video display is a graphic representation of heart rate.

BRIEF SUMMARY OF THE INVENTION

A modified universal infra-red (IR) remote controller for television and audio components which is triggered by its user's heart rate.

The object of the invention is to provide a more powerful motivation (entertainment) for optimal exercise (target heart rate training) in a simpler, more universally adaptable and less expensive form than is found in the prior art.

The present invention specifically improves upon the prior art by incorporating heart rate target training and passive entertainment and by being independent of bulky and expensive exercise equipment. It provides a variable and continuous form of feedback in the form of entertainment volume changes.

Being able to enjoy audio/visual entertainment rewards the user. Heart rate target training goals are the basis for establishing optimal exercise.

A user simply exercises, with or without any type of exercise equipment and watches TV or listens to their stereo. A heart rate monitor combined with a transmitter sends data to a nearby control unit. Within the control unit, a proprietary microprocessor commands the control unit to alter the volume or power settings on the entertainment device in accordance with pre-programmed parameters and individualized user settings for age and intensity level. If the user's heart rate moves below or above the recognized target range, volume is gradually altered, i.e. ramped down or ramped up, and ultimately power interrupted until the user reacquires the target range.

There are examples in the prior art of heart rate sensing devices controlling exercise equipment or video games. The field is also crowded with examples of speed sensing exercise devices to control electronic equipment. none of the prior art incorporates the benefits of heart rate target training with the simple motivational reward of watching television or listening to music. Further, the present invention is usable with any exercise equipment or none at all, is simple, lightweight and less expensive to produce than those found in the prior art.

DETAILED DESCRIPTION OF THE INVENTION

Figure 1:
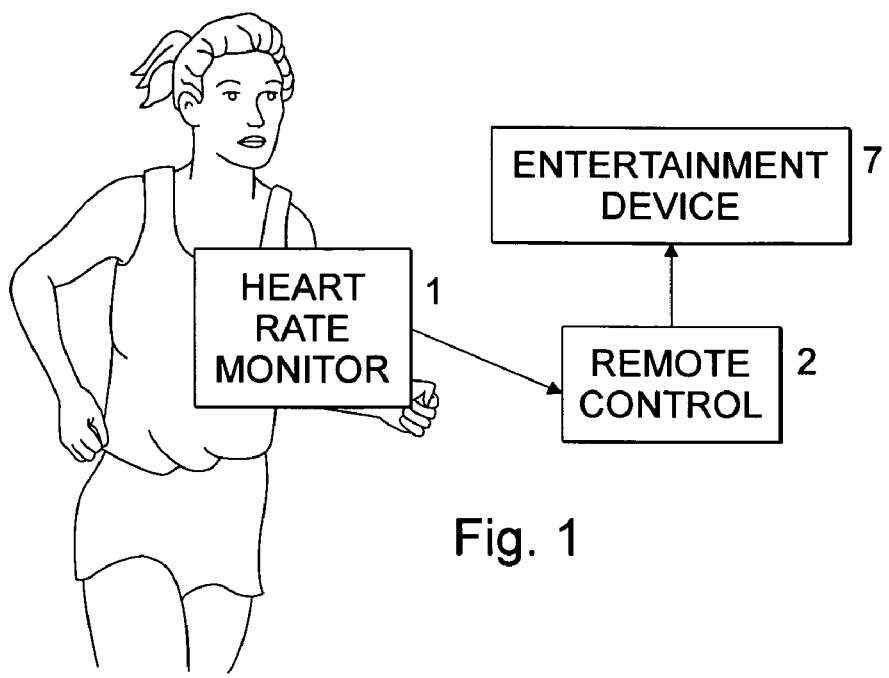
FIG. 1 illustrates the concept of controlling entertainment devices with a heart rate monitor.
Figure 2:
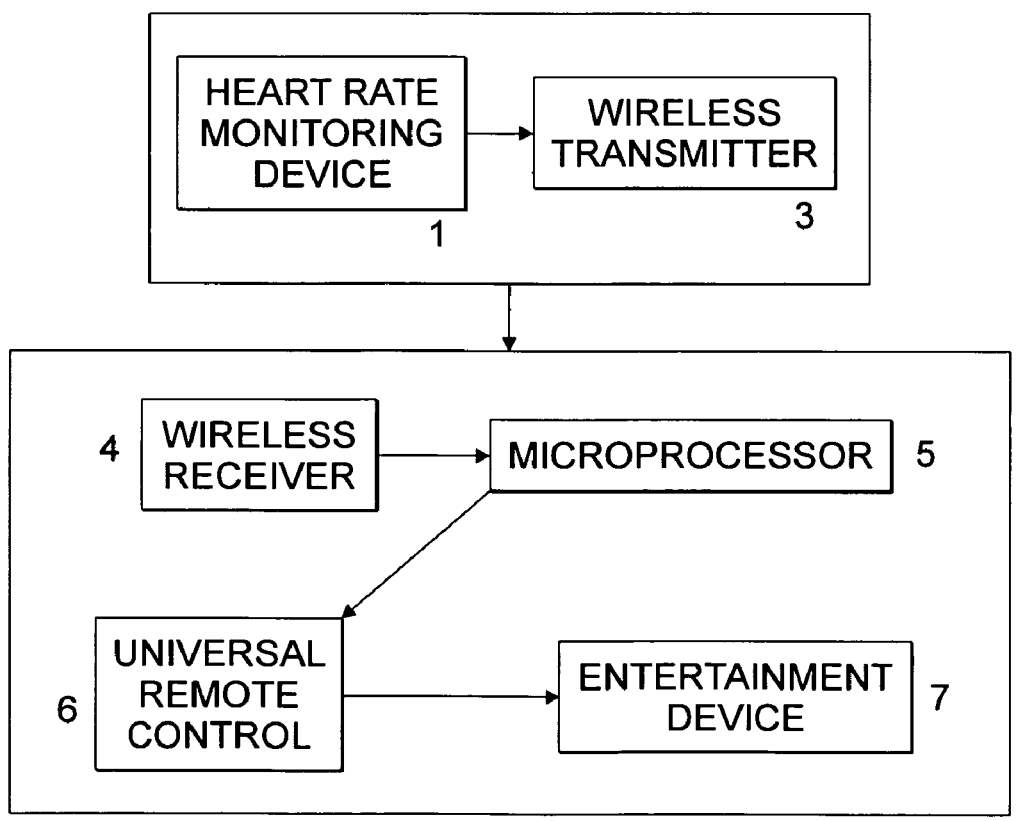
FIG. 2 shows a first embodiment of apparatus of the present invention for controlling a stand-alone entertainment device and the components from which it is comprised.
Figure 3:
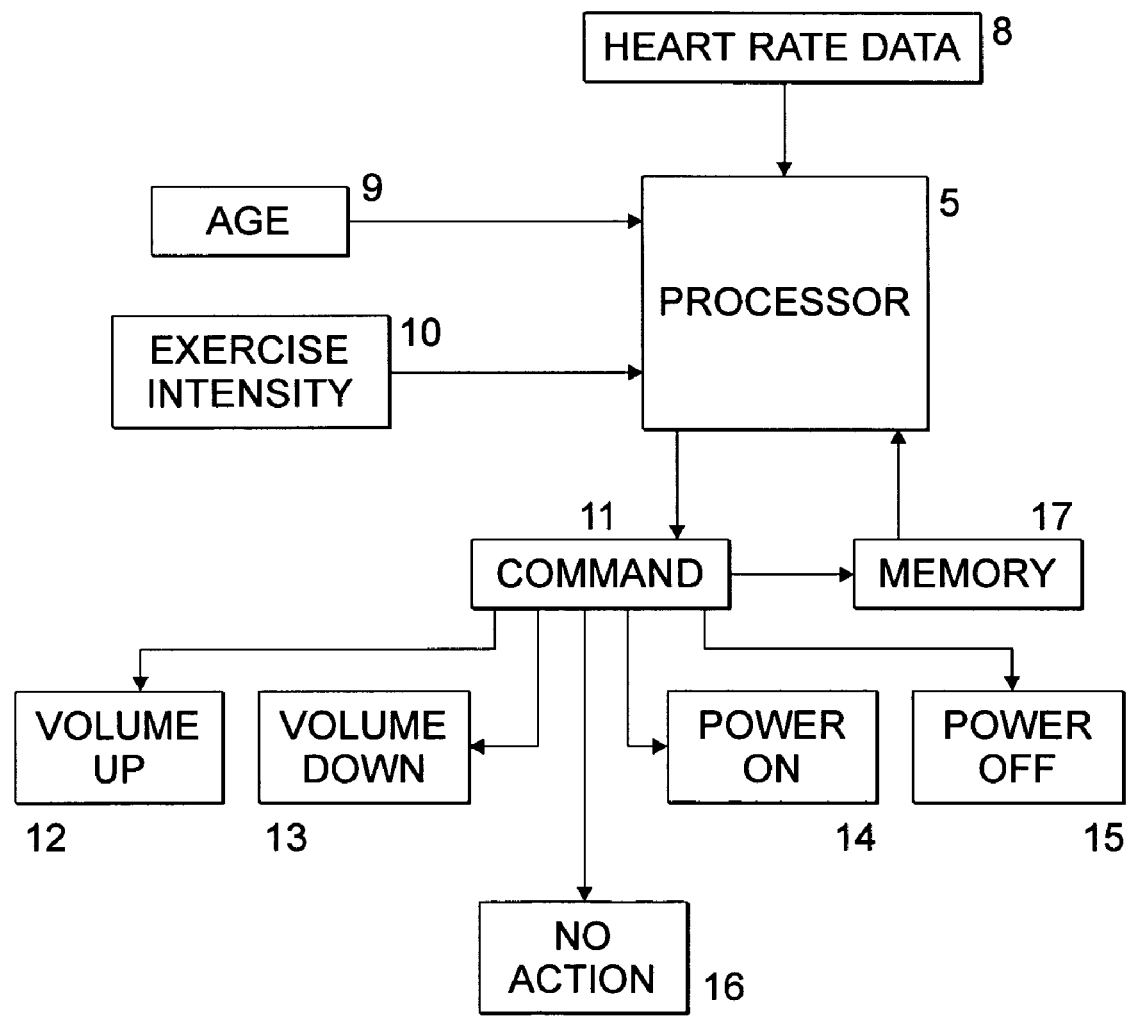
FIG. 3 is a flow chart of the logic used by the microprocessor of FIG. 2.

In the first embodiment, a chest strap type of heart rate monitor 1, such as those manufactured by Polar, is modified to transmit wireless heart rate data 3. The remaining functions are carried out by several components contained within a controller unit 2, which are interconnected by electronic circuitry. The controller unit 2 receives the heart rate data 4. That data is fed to a microprocessor 5 which is programmed to compare it with a desired target range at regular time intervals. Based on that comparison, the microprocessor will send a command (or not) to the universal remote control 6 to send volume control and power control signals to the entertainment device 7. The control unit must be in a line of sight to the entertainment device to allow for uninterrupted remote control.

Figure 4:
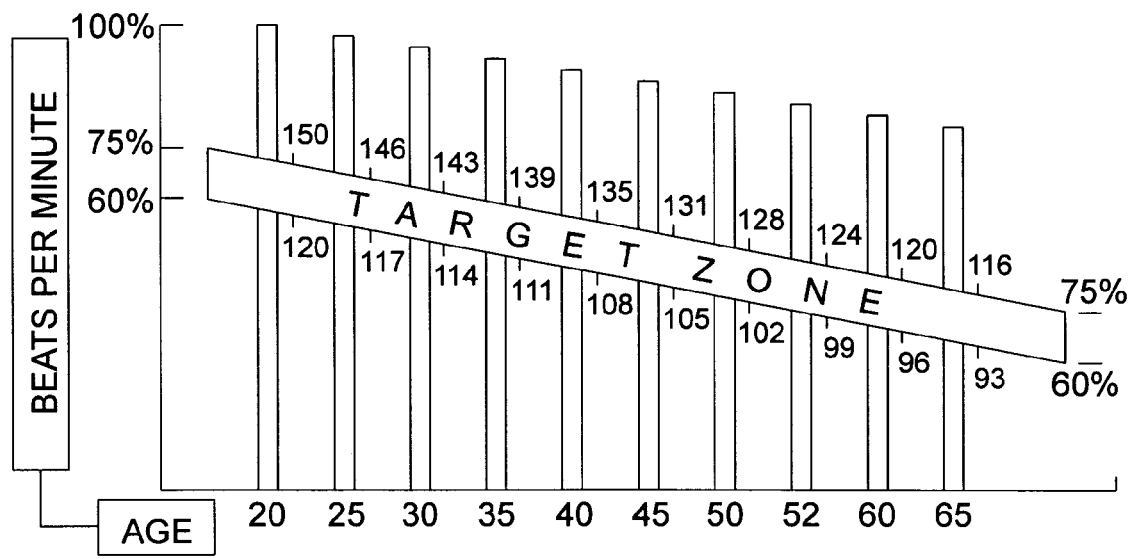
FIG. 4 shows a graphic table of target training heart rates.

The processor 5 receives heart rate data 8 and compares it to the target rates described in FIG. 4, which are conditioned by the user inputs for age 9 and exercise intensity 10. The processor 5 sends a command 11 at periodic intervals. The command may be either volume up 12, volume down 13, power-on 14, power-off 15 or no action 16. Each command during the exercise period is tracked by the memory 17 which further conditions the commands sent by the processor 5.

The processor keeps track of all commands sent to the entertainment device 7 so that it may condition each new command based upon the current status of the entertainment device. The processor has no direct feedback from the entertainment device and thus begins its calculations with an understood zero baseline volume level. This corresponds to the comfortable listening volume on the entertainment device set by the user prior to commencing exercise. So, for example-down if the processor calculates that there is only one command or a total of volume-down commands and the user's heart rate is still below target at the next periodic interval, the processor will send another volume-down command. If, however, the prior command was to inactivate the audio output, and the user has reacquired the target, a command to reactivate the audio output would be sent.

Although the preferred embodiment described above is specific for purposes of illustration, other permutations of the combination heart rate monitor and universal remote control are possible within the spirit and scope of the invention. For example, the chest strap heart rate monitor may be replaced with other types of heart rate monitoring devices, such as finger cots or clips, ear clips, arm bands, etc. The wireless features may employ various technologies or be replaced with hard-wired connectivity. And, the logic used by the microprocessor to effect the desired result of motivating heart rate target training exercise by controlling an entertainment device, may vary in possible permutations of the invention. These variations are embodied in the second and third embodiments of the invention illustrated in FIGS. 5 and 8.

Figure 5:
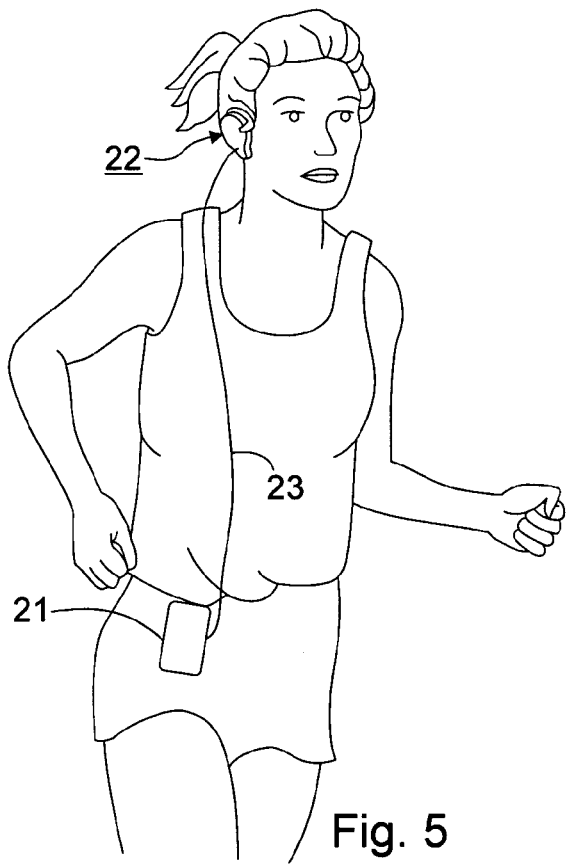
FIG. 5 is a view similar to FIG. 1 illustrating a second embodiment of apparatus of the invention for controlling a portable entertainment device which may be carried during exercise.
Figure 6:
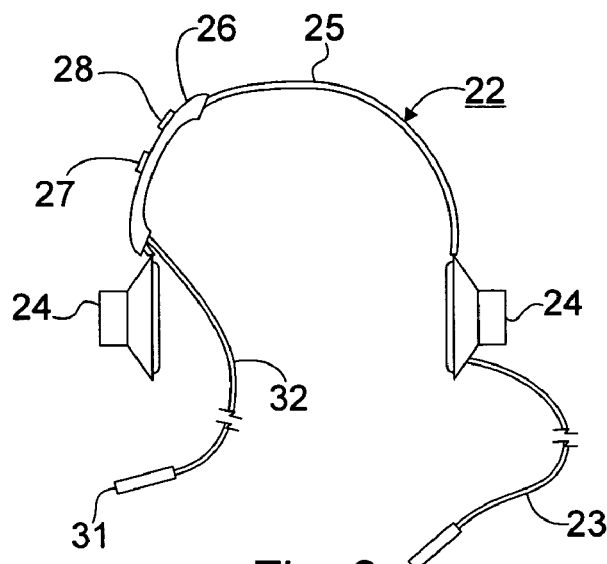
FIG. 6 is a view of a headset which may be used in the apparatus of FIG. 5.
Figure 7:
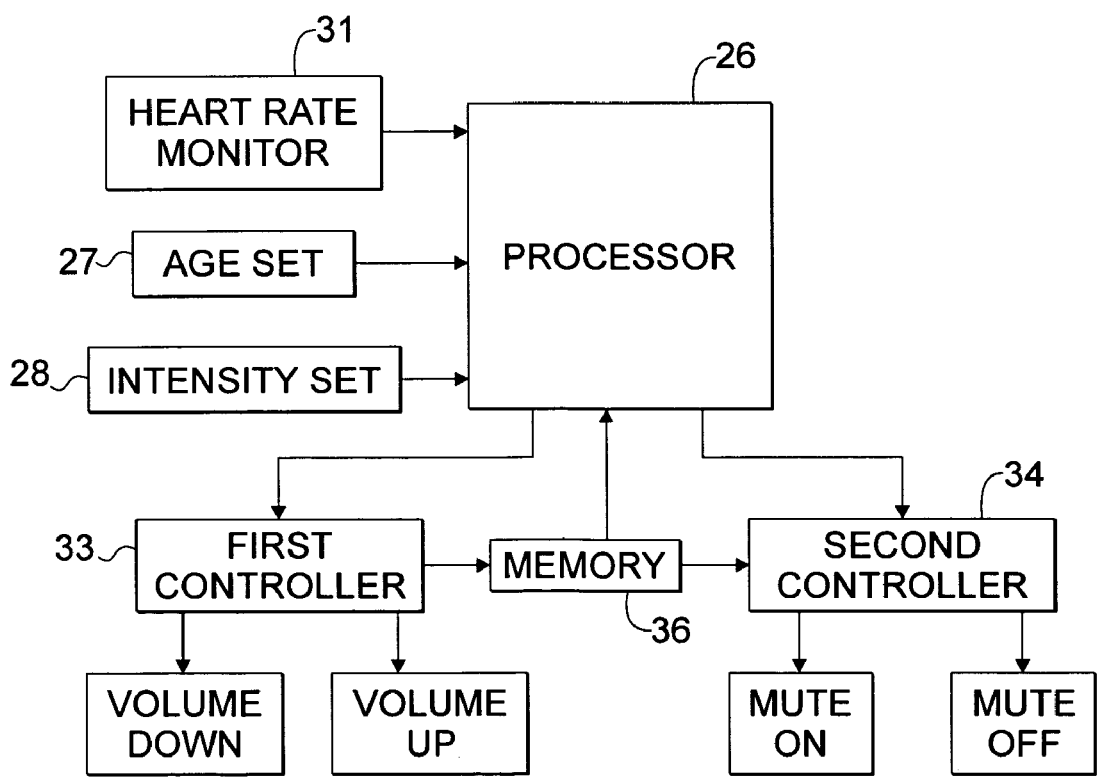
FIG. 7 is a flow chart of the logic used in the apparatus of FIGS. 5 and 6.

As shown in FIG. 5, the second embodiment uses a portable entertainment device such as a music player which may be carried by the person for example, either in the hand, in a pocket, or attached to a belt or waistband, as shown in FIG. 5 at 21. The audio output may emanate either from speakers in or attached to the unit or through earphones as indicated in FIG. 5. The headset is coupled to the player 21 by a coupling 23, in the present instance a conventional plug-in cord. As shown in FIG. 6, the headset 22 has a pair of earphones 24,24 which are adapted to be held against the ears of the person by a headband 25.

A processor 26 is provided to control the audio output of the earphones 24. In the present instance, the processor 26 is also mounted on the headband 25 and includes adjusting devices 27 and 28 for setting the age of the person and the desired intensity of exercise respectively. A heart rate monitor 31 is coupled to the processor 26, in the present instance by a hard wire connector 32. An ear clip may be clipped to the ear of the person adjacent to one of the earphones 24. The ear clip may be replaced by a chest strap heart rate monitor, a finger cot or clip, an arm band, or the like.

The processor is coupled to a first controller 33 which is effective to increase or decrease the volume of the audio output and a second controller 34 which turns the audio output on or off, either by muting or by interrupting the power source.

As in the first embodiment, the processor establishes a target range of data and periodically receives the heart rate data from the monitor 31 for comparison with the target range and generates a command to one or both of the first and second controllers 33 and 34. When the heart rate falls below the target range, the controller 33 ramps down the volume, and when the heart rate goes above the target range, the controller 33 ramps up the volume. The processor may also establish a second target range which has limits beyond the said target range so that when the heart rate either exceeds or falls below the second target range, the controller 34 will interrupt the audio output completely. The commands are also fed into a memory component 36 which feeds back data to the processor to keep track of the command and generate new commands based on the status of the audio output. This feedback enables the second controller 34 to reactivate the audio output when the heart rate monitor provides data indicating the heart rate is again within the target range.

If it is desired to use the second embodiment in connection with a portable entertainment device which cannot be readily carried by the person, the hard-wired couplings described above may be replaced by infrared couplings as described in connection with the first embodiment.

Within the scope of the invention, the first controller may modulate the audio output in ways other than modulating the volume. For example, if the entertainment device has multiple outputs, the first controller may modulate the output by selecting a different output rather than changing the volume.

The varied target ranges available to the user are based upon generally accepted targets outlined in the graph in FIG. 4. In the first and second embodiments, these target ranges are further altered by the processor in response to user settings for age and exercise intensity. The user switches exercise intensity to either "fat burning" or "cardio-fitness". For example, a 40-year old desiring optimal target training for weight loss would set the age switch to 40 and the intensity to fat burning. That person could alternatively set the intensity switch to cardio-fitness for a more strenuous workout.

Figure 8:
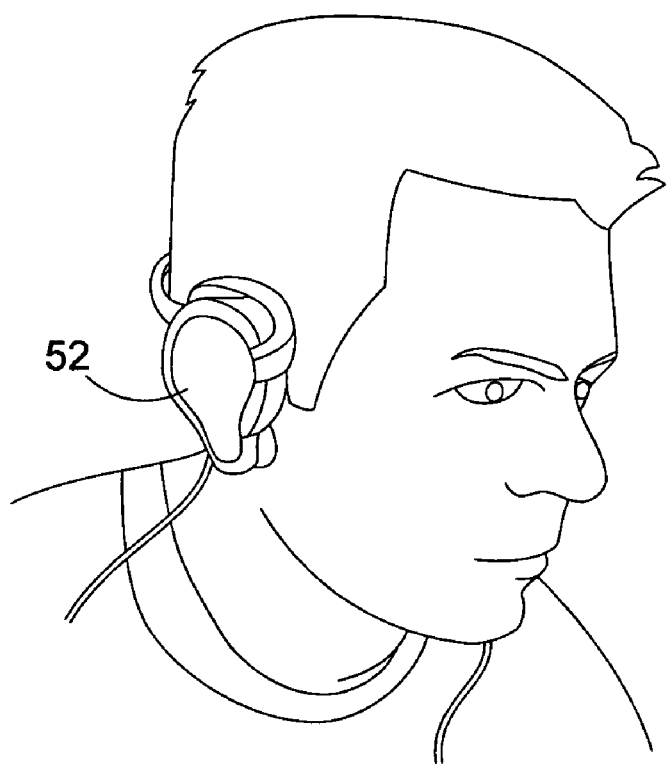
FIG. 8 is a view showing a third embodiment of the invention mounted on the head of a person.
Figure 9:
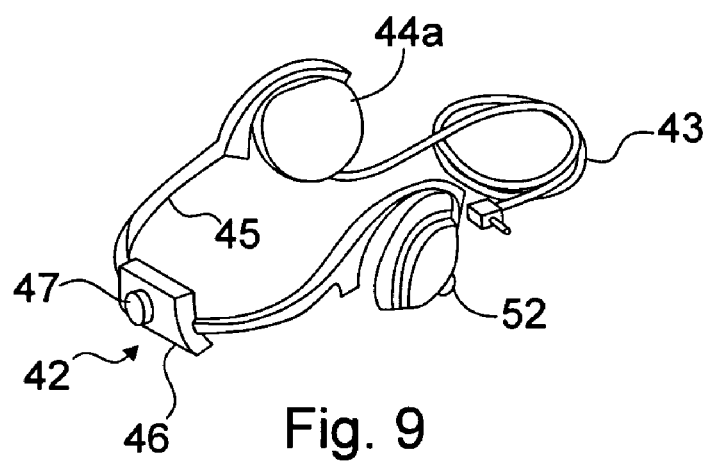
FIG. 9 is a view of the headset apparatus shown in FIG. 8 removed from the person.
Figure 10:
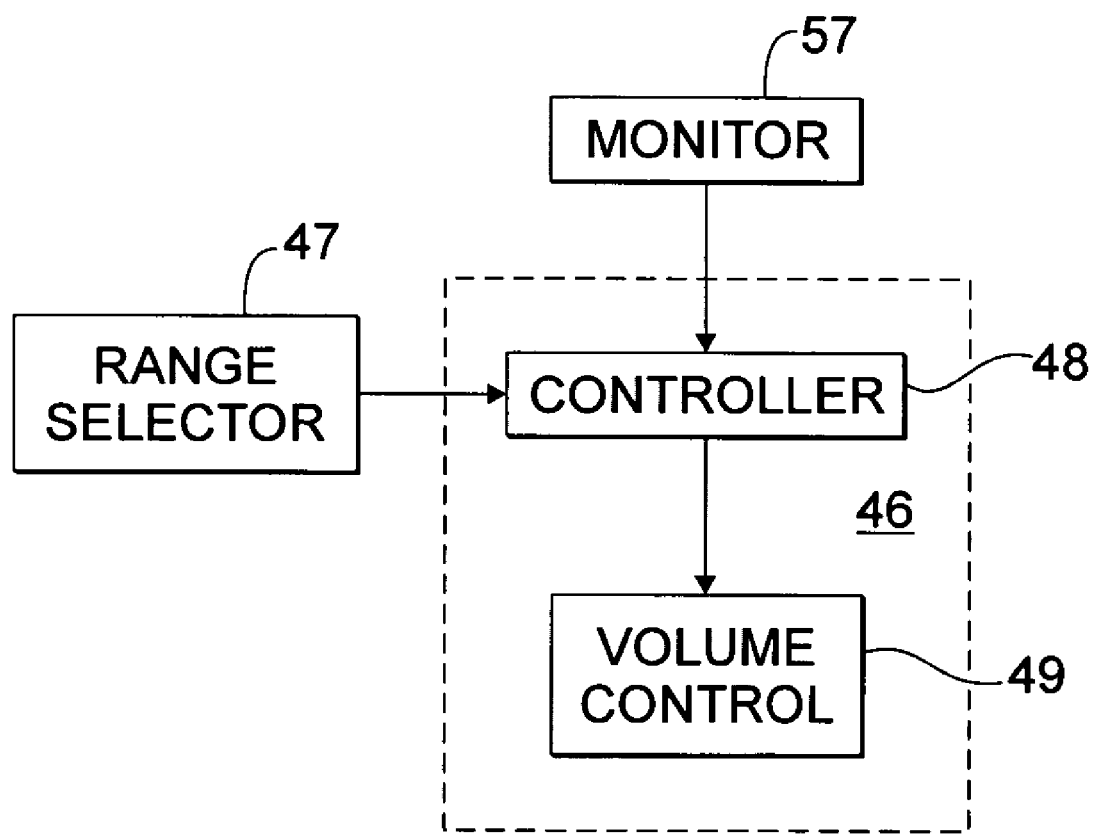
FIG. 10 is a flow chart of the logic used in the apparatus of FIGS. 7 and 8.

A third embodiment of the invention is illustrated in FIGS. 8-10. In this embodiment, a headset 42 shown in FIG. 9 replaces the headset 22 of the second embodiment. The headset 42 is coupled to the player (not shown) by a coupling in the form of a conventional plug-in cord 43. The headset mounts a pair of earphones, 44a, 44b, which are adapted to be held against the ears of the person by a headband 45.

A processor 46 is provided to control the audio output of the earphones 44. In this embodiment, the processor 46 is mounted on the headband and includes an adjustment 47 for setting the target range. In the present instance, the settings for the target range are identified by the heart rate at mid range, and the target range will embrace heart rates within a few heartbeats on either side of the mid range. A heart rate monitor 51, in the present instance, comprising an ear clip 52, is mounted on an earphone, in the present instance, the earphone 44b, and is designed to output the heart rate of the person to the processor 46 through a hard wire connection in the headband 45. The processor 46 includes a controller 48 and a volume control 49 which is coupled to the earphones 44a and 44b by hard wiring in the headband 45. The volume control 49 is effective to increase or decrease the volume of the audio output of the earphones. When the monitored heart rate falls below the target range, the volume is ramped down, and when the heart rate falls above the target range, the volume control 49 ramps up the volume of the audio output. The monitor and/or the controller is effective to compare the person's heart rate with the target range periodically so that if the person does not moderate the intensity of their exercise, the volume control is effective to continue the modulation of the audio output, either ramping it down to a point where it is inaudible or ramping it up to a point it is obvious that the person should interrupt their exercise.

EXAMPLE OF PRACTICAL USE

Before exercising, the user sets the control unit to communicate with their chosen entertainment device. To exercise, the user turns on a desired television or audio program and sets a comfortable baseline listening volume. They then activate the apparatus and commence exercise. Within the apparatus, the processor may start a clock. After a warm-up period, the processor begins, at periodic intervals, to sample the user's real-time heart rate and compare it to the target range. The user may comfortably enjoy their entertainment as long as their heart is beating in the desired range. The user is quickly motivated to correct their exercise intensity by the modulation of the audio output condition of the entertainment device.

The invention claimed is:

1. Motivational fitness apparatus for a person to use while exercising with an entertainment device having a power supply, at least an audio output operable to be set at a given volume which is a comfortable listening volume, said apparatus comprising:
   a controller for ramping up and ramping down the audio output above and below said given volume,
   a processor operable to generate a command signal directed to said controller, and
   a monitor operable to generate heart rate data of the person,
   said processor operable to first establish a target range of data, and second to receive said heart rate data from said monitor and periodically compare said data with said target range of data, and to generate a command indicative of the variation of said heart rate data relative to said target range, and to direct said generated command to said controller, said command operable to ramp up the volume of the audio output above said given volume when the heart rate data is above said target range and to ramp down the volume of the audio output below said given volume when the heart rate data is below said target range.

2. Apparatus according to claim 1 wherein said processor is operable to establish a second target range which has limits beyond said first target range, and then to compare said data with first and second target ranges and to generate a first command upon comparison with the first of said ranges, and a second signal upon comparison with the second of said ranges, said first command being directed to said controller for ramping up or ramping down the audio output and the second signal deactivating the audio output.

3. Apparatus according to claim 2 wherein said processor includes a setting device operable by the person to selectively adjust said first and second target ranges.

4. Apparatus according to claim 1 including a head-mounted listening component coupled to the entertainment device.

5. Apparatus according to claim 4 including a headset mounting said listening component, wherein said processor is mounted on said headset, and
   said monitor comprises an ear clip adapted to provide the person's heart rate data to said processor.

6. Apparatus according to claim 5 wherein said listening component comprises at least one earphone carried by said headset, said earphone having an audio output controlled by said controller and mounting said ear clip.

7. A method for motivating a person doing fitness exercises comprising the steps of:
   providing an entertainment device having a power supply, at least an audio output operable to be set at a given output which is a comfortable listening output, and a processor, a controller for modulating audio output and a heart rage monitor;
   generating at least one command directed to said controller;
   monitoring the heart rate of the person and generating heart rate data of the person,
   comparing said heart rate data with a target range of data, and causing said command to be indicative of the variation of said heart rate data relative to said target range, and
   using said generated command to ramp down or ramp up the volume, or deactivate or reactivate the audio output, said command ramps down the volume of said audio output when the heart rate falls below said target range and ramps up the volume when the heart rate rises above the target range.

8. A method according to claim 7 wherein said generating step also generates a second command which deactivates the audio output when the heart rate falls outside the target range.

9. A method according to claim 8 wherein said generating step also generates a third command which reactivates the audio output when the heart rate falls back into the target range after falling outside the target range.

* * * * *